(12) United States Patent
Huber

(10) Patent No.: US 7,414,138 B2
(45) Date of Patent: Aug. 19, 2008

(54) BENZOXAZOLE AND BENZODIAZOLE UV-A SUNSCREENS

(75) Inventor: Ulrich Huber, Erlenbach (CH)

(73) Assignee: DSM IP Assets B.V., TE Heerlen (NL)

( * ) Notice: Subject to any disclaimer, the term of this patent is extended or adjusted under 35 U.S.C. 154(b) by 693 days.

(21) Appl. No.: 10/518,604

(22) PCT Filed: Apr. 8, 2003

(86) PCT No.: PCT/EP03/03634

§ 371 (c)(1), (2), (4) Date: Dec. 17, 2004

(87) PCT Pub. No.: WO04/000256

PCT Pub. Date: Dec. 31, 2003

(65) Prior Publication Data

US 2005/0260144 A1   Nov. 24, 2005

(30) Foreign Application Priority Data

Jun. 25, 2002 (EP) .................... 02014158

(51) Int. Cl.
| | |
|---|---|
| C07D 263/00 | (2006.01) |
| C07D 413/00 | (2006.01) |
| C07D 235/00 | (2006.01) |
| A01N 43/00 | (2006.01) |
| A01N 43/76 | (2006.01) |
| A61K 31/42 | (2006.01) |
| C07D 263/56 | (2006.01) |
| C07D 498/00 | (2006.01) |
| C07D 239/48 | (2006.01) |
| C07D 237/36 | (2006.01) |
| C07D 239/93 | (2006.01) |
| C07D 235/18 | (2006.01) |
| C07D 239/66 | (2006.01) |
| C07D 239/56 | (2006.01) |
| C07D 235/22 | (2006.01) |
| A61K 31/00 | (2006.01) |
| A61K 31/415 | (2006.01) |
| A01N 43/52 | (2006.01) |

(52) U.S. Cl. .............. 548/224; 548/310; 548/310.4; 548/310.7; 514/375; 514/394; 514/395

(58) Field of Classification Search ........... 514/375, 514/394, 395; 548/224, 310.1, 310.4, 310.7
See application file for complete search history.

(56) References Cited

U.S. PATENT DOCUMENTS

2001/0053856 A1   12/2001   Leduc et al.

FOREIGN PATENT DOCUMENTS

| EP | 832 641 | 4/1998 |
| EP | 921 126 | 6/1999 |

OTHER PUBLICATIONS

Park, K.H. et al., "Second-Order Nonlinear Optical Polymers Based on Benzoxazole Chromophores," *Nonlinear Optics.*, vol. 20, pp. 73-86 (1999).

*Primary Examiner*—Johann Richter
*Assistant Examiner*—Courtney A Brown
(74) *Attorney, Agent, or Firm*—Bryan Cave LLP

(57) ABSTRACT

The present invention relates to 1,3-benzoxazole or benzodiazole UV-A sunscreens and to compositions, in particular topical compositions, containing the above UV-A sunscreens.

15 Claims, No Drawings

BENZOXAZOLE AND BENZODIAZOLE UV-A SUNSCREENS

This application is the National Stage of International Application No. PCT/EP2003/003634, filed Apr. 8, 2003.

The present invention relates to novel UV-A sunscreens and to compositions, in particular topical compositions, containing the above UV-A sunscreens.

Depending on the wavelength, UV rays are designated as UV-A rays (320-400 nm) and UV-B rays (280-320 nm). The damaging action of the UV rays on the human skin increases with decreasing wavelength and increasing duration of exposure. UV rays can thus cause skin damage, it being possible for UV-B radiation to cause sunburn (erythema) up to very severe skin burns. Very frequent and unprotected irradiation of the skin with sunlight also leads to a loss in skin elasticity and to increased wrinkle formation and on the whole to premature aging of the skin. In extreme cases pathological skin changes up to skin cancer can occur.

The UV-A radiation causes a rapid, weak direct pigmentation of the skin. UV-A rays penetrate into deeper skin layers and there can accelerate the aging process of the skin. The UV-A radiation can furthermore elicit phototonic or photoallergic skin reactions. Confirmed relationships exist between UV-A exposure and increased risk of skin cancer. According to the position of their absorption maxima, UV absorbers for cosmetic and dermatological preparations are divided into UV-A and UV-B absorbers. While there are a large number of safe and effective UV-B absorbers, UV-A absorbers suitable for the protection of human skin are rare and, moreover, affected by serious disadvantages EP-A1-669 323, DE-3644633, DE 4107439 disclose, for instance, benzo-diazoles, -thiazoles and/or benzoxazoles absorbing in the UV-A range. The compounds according to these prior art documents, which compounds strongly differ in their chemical structure from those according to the present invention, show low liposolubility. This is a serious drawback since UV-sunscreens must usually be incorporated into the lipid phase of the cosmetic and/or dermatological composition in order to assure an optimal absorption into the skin.

Furthermore, the UV-A sunscreens of the cited prior art usually do not show photostability. This is an additional drawback since they loose their activity when exposed to the sun light.

The object at the root of the present invention is to provide UV-A sunscreens overcoming the drawbacks mentioned above, i.e. UV-A sunscreens with good liposolubility and high photostability.

This object is achieved by providing compounds of general formula I

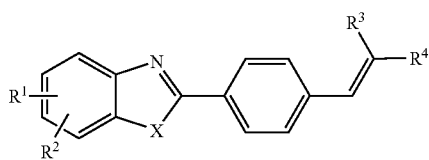

I wherein
$R^1$ and $R^2$ are, independently from each other, hydrogen; halogen; hydroxy; $(C_1-C_{20})$-alkyl; $(C_2-C_{20})$-alkenyl; or $(C_1-C_{20})$-alkoxy;
X is oxygen or an imino group, optionally substituted with $R^1$;
$R^3$ and $R^4$ are, independently from each other, cyano; —$COOR^5$; —$COR^6$; —$CONH_2$; —$CONHR^7$; or —$CONR^8R^9$;
$R^5$, $R^6$, $R^7$, $R^8$ and $R^9$ are, independently from each other, hydrogen; $(C_1-C_{20})$-alkyl, wherein one or more methylene groups are optionally replaced by oxygens; $(C_1-C_{20})$-haloalkyl; $(C_2-C_{20})$-alkenyl, optionally substituted by tri-$(C_1-C_5)$-alkylsilyl or triphenylsilyl or a group -$Si[CH_3]_n[OSi(CH_3)_3]_{3-n}$, wherein n is 0, 1, 2 or 3.

The compounds of general formula I are valuable, photostable products which have their absorption maxima in the UV-A range. They are moreover lipophilic and, therefore, suitable for being incorporated into the lipid phase of sun screen formulations.

As used herein, $C_1-C_{20}$-alkyl denotes straight chain or branched chain alkyl residues with 1 to 20 carbon atoms, such as methyl, ethyl, propyl, isopropyl, thexyl (=1,1,3,3-tetramethyl-butyl), 1,1,2-trimethylpropyl, n-butyl, sec.-butyl, tert.-butyl, pentyl, neopentyl, hexyl, 2-ethyl-hexyl, octyl and the like. $C_1-C_8$-Alkyl groups are preferred.

$C_2-C_{20}$-Alkenyl denotes straight chain or branched chain alkenyl residues with 2 to 20 carbon atoms and containing at least one C—C double bond, such as vinyl, allyl, 2-butenyl, methallyl, 2-penten-3-yl, 3-hexen-2-yl, 3-hepten-2-yl, 3-octen-2-yl, 1-octen-3-yl and 2-octen-1-yl. $C_2-C_8$-Alkenyl groups are preferred.

Examples of "$(C_1-C_{20})$-alkyl wherein one or more methylene groups are optionally replaced by oxygen" are methoxymethyl, 4-oxa-hexyl, 4,7-dioxa-nonyl and 4,7,10-trioxa-dodecyl.

A tri-$(C_1-C_5)$-alkylsilyl moiety is a group —$SiR^aR^bR^c$, wherein $R^a$, $R^b$ and $R^c$ each independently are $C_1-C_5$-alkyl. Preferred silyl moieties are trimethylsilyl, triethylsilyl, tripropylsilyl, triisopropylsilyl, dimethyl-tert.-butyl-silyl, dimethyl-thexyl-silyl, and the like. Preferred trisubstituted silyl groups are trimethylsilyl, triethysilyl and triphenylsilyl.

The compounds of general formula I can be prepared by condensation of a compound of general formula IIIa (if X is O) or IIIb (if X is NH or $NR^1$)

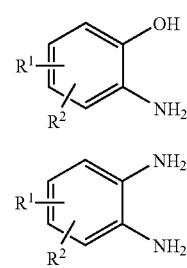

IIIa

IIIb with a compound of general formula IV

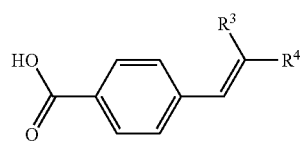

IV wherein $R^1$, $R^2$, $R^3$ and $R^4$ have the meanings given above.

The condensation with heterocyclic ring formation is carried out in the presence of an acidic catalyst. Any strong anorganic or organic acid, such as $H_2SO_4$, HCl, $H_3PO_4$, $H_3BO_3$, or p-toluenesulfonic acid, can be used for this purpose. The water formed by the reaction can be removed by azeotropic destination (e.g using toluene or $CH_2Cl_2$ as a solvent) or by means of a hygroscopic agent such as $P_2O_5$. The reaction temperature may vary between 0° C. and 200° C. and depends on the concentration and strength of the acid.

The starting material of general formula IV can be obtained by means of a Knoevenagel condensation, i.e., by reacting a compound of general formula V, optionally in the form of an ester built with an alkanol, with a compound of general formula VI:

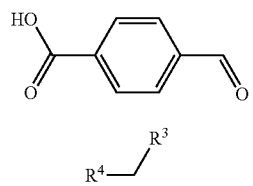

V

VI

The condensation may take place, e.g., under azeotropic destination in the presence of a solvent capable of forming an azeotrope with water (e.g. toluene or chloroform) and of a water separator. Acids and/or bases can be used as catalyst: acids like acetic acid, benzoic acid, toluenesulfonic acid, sulfuric acid, $BF_3$, or bases like pyridine, piperidine or morpholine. Anhydrides like $P_2O_5$ can also catalyze the reaction.

A compound of general formula I can also be manufactured by inverting the order of the above steps, i.e. by reacting a compound of general formula VII with a compound of general formula VI

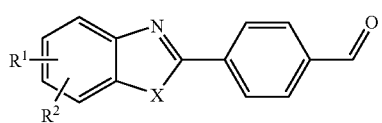

VII

A compound of general formula VII, on its turn, can be obtained by reacting a compound of general formula IIIa (X=O) or IIIb (X=NH or $NR^1$) with a compound of general formula V. The general reaction conditions are the same as for the ring closure described above.

Preferred compounds of formula I are those wherein X is O. Furthermore, particularly preferred compounds are those wherein $R^1$ and $R^2$ are hydrogen, as well as those wherein $R^3$ is cyano and $R^4$ is —$COOR^5$. Examples of such compounds are:

2-Cyano-3-{4-[5-tert.-butyl-benzoxazol-2-yl]-phenyl}-acrylic acid 2-ethylhexyl ester and 2-Cyano-3-{4-benzoxazol-2-yl-phenyl}-acrylic acid 2-ethylhexyl ester.

Compounds wherein $R^3$ and $R^4$ are independently from each other —$COOR^5$ are also preferred. Examples of such compounds are:

2-(4-Benzoxazol-2-yl-benzylidene)-malonic acid diethyl ester;

2-(4-Benzoxazol-2-yl-benzylidene)-malonic acid dibutyl ester;

3-{4-Benzoxazol-2-yl-phenyl}-2-propionyl-acrylic acid 2-ethylhexyl ester;

2-(4-[6-Hydroxy-benzoxazol-2-yl]-benzylidene)-malonic acid diethyl ester;

2-(4-[6-{2-Ethyl-hexyloxy}-benzoxazol-2-yl]-benzylidene)-malonic acid diethyl ester; and 2-(4-{6-[2-(2-Ethoxy-ethoxy)-ethoxy]-benzoxazol-2-yl}-benzylidene)-malonic acid diethyl ester.

In another aspect, the present invention relates to substituted polysiloxanes of the general formula $(H_3C)_3Si—(B)_q—OSi(CH_3)_3$  II wherein B is a residue selected from the group consisting of B1, B2, B3, B4 and B5;

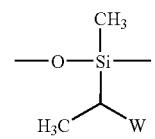

B1

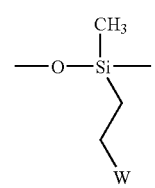

B2

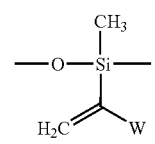

B3

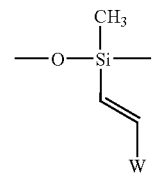

B4

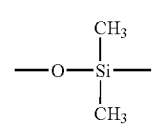

B5

W is a residue from the group consisting of W1, W2 and W3

W1
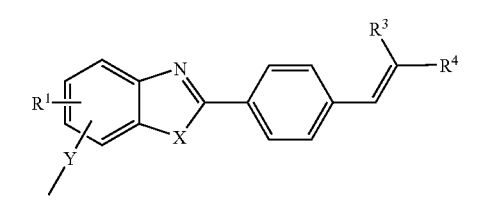

W2
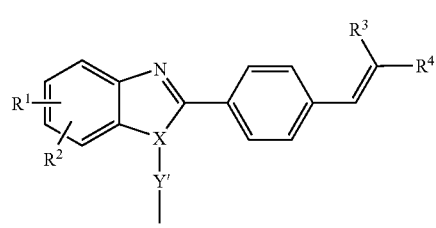

W3
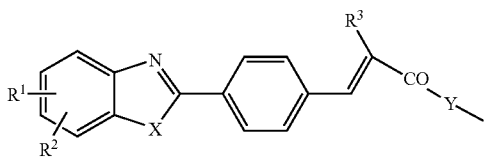

wherein X, R1, R2, R3 and R4 are as defined above; Y is oxygen, $(C_1-C_{20})$-alkylene, $(C_2-C_{20})$-alkenylene, or —O—$(C_1-C_{20})$-alkylene; and Y' is $(C_1-C_{20})$-alkylene or $(C_2-C_{20})$-alkenylene.

q is an integer between 1 and 400 and represents the sum of residues B1 to B5 in arbitrary sequence, wherein at least one B is B1, B2, B3 or B4, the ratio $(B1+B2+B3+B4)/(B1+B2+B3+B4+B5)$ not exceeding 0.6.

Preferred polysiloxanes of formula II are those wherein q is in the range between 2 and 100. Particularly preferred polysiloxanes of formula II are those for which the ratio (B1+B2+B3+B4)/(B1+B2+B3+B4+B5) is between 0.01 and 0.4.

A preferred polysiloxane of formula II is

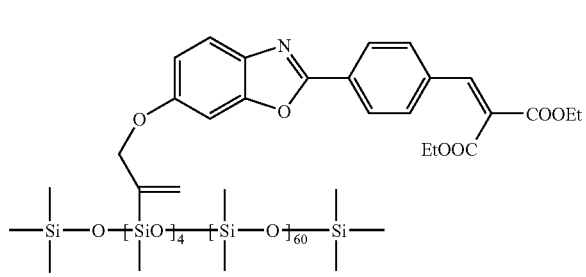

The compounds of general formula II can be prepared by grafting a compound of formula VIII VIIIaa
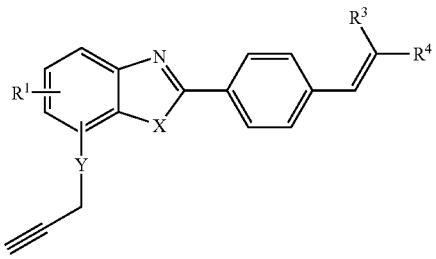

VIIIab
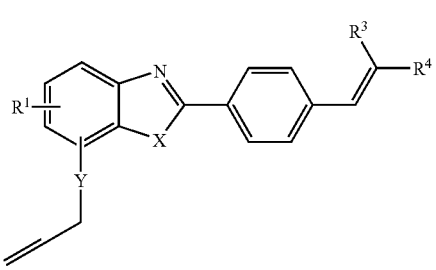

VIIIba
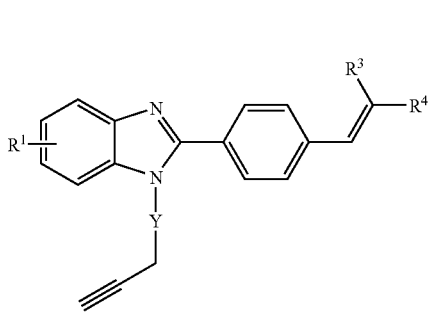

VIIIbb
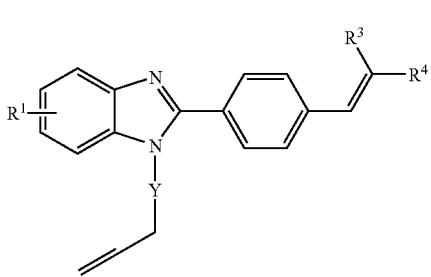

VIIIca
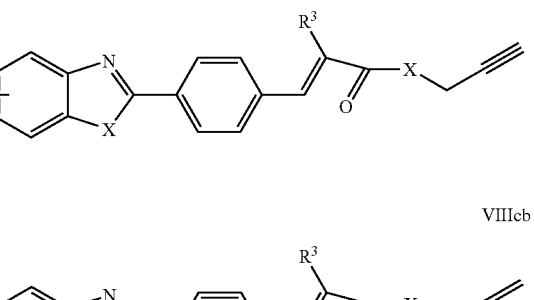

VIIIcb
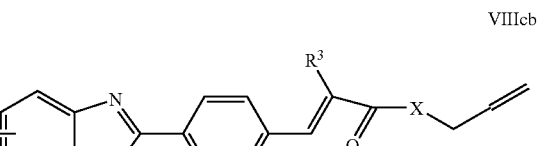

onto a poly-(methyl-hydrosiloxane)

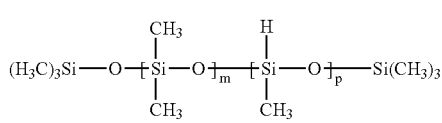

wherein m+p=q,
q being as defined above
and the different residues are in arbitrary sequence It is evident that the molar ratio of the reaction partners is determined by the hydrid content, i.e. content of groups —Si[H][CH₃]—O—, of compound IX.

Typically, the reaction takes place in the neat polysiloxane or in a polysiloxane solution in, e.g.) toluene, THF or isopropanol The reaction may take place in the presence of homogeneous catalysts (Karstedt catalyst) or a heterogeneous platin catalyst (chloroplatinic acid), at a temperature between 40 and 150° C., preferably between 60 and 100° C., and for a period of time varying between 2 and 48 hours.

The compounds of formulae VIIIaa and VIIIab can be obtained by treating a compound of formula VII wherein $R^2$ is OH with a) proparagyl bromide or b) with allylbromide, respectively, using a base (e.g. KOH or $K_2CO_3$) at 50 to 150° C. in a polar aprotic solvent like, e.g., N-methylpyrrolidone or butanone. This new compound of formula VIIaa ox VIIab can be treated with a compound VI as described above. The compounds of formulae VIIba and VIIIbb can be obtained accordingly under the above conditions starting from compound VII wherein X is NH or $NR^1$. The compounds of formulae VIIIca and VIIIcb can be obtained by treating a compound of formula VI wherein $R^3$ is CN and $R^4$ is $COOR^5$ (compound VI') to give a compound of formula VI" or VI'", respectively, before reacting them with compound VII as described above.

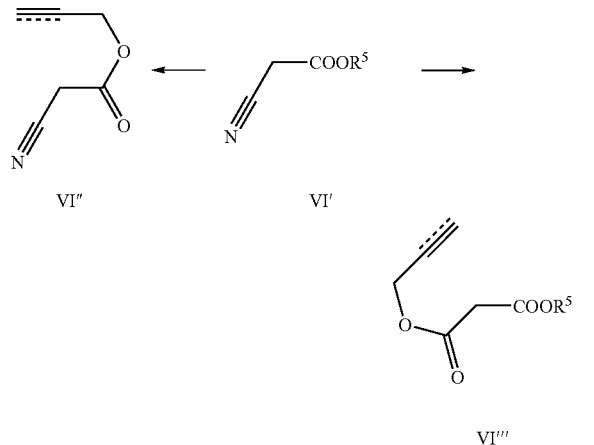

===== means a double or a triple bond

To obtain compound VI", compound VI' treated with dry HCl or conc. $H_2SO_4$ at room temperature followed by addition of propynol or propenol, respectively, and hydrolysis of the immonium salt intermediate. Compound VI'" is formed from compound VI' by transestenfication, using excess of propynol or propenol, respectively.

A further aspect of the present invention concerns the use of one or more compounds of formulae I and/or II as an UV-A screening agent. In particular, the compounds of general formulae I and/or II are suitable for protecting human skin and/or human hair from UV-A irradiation, as well as for protecting UV sensitive plastic materials and medicinal products.

It is still a further aspect of the present invention to provide a composition, in particular a topical composition, containing one or more compounds of formulae I and/or II and at least one pharmaceutically and/or cosmetically acceptable excipient.

The compositions comprising one or more compounds of formulae I or II are particularly suitable for topical applications onto human skin and/or hair. Accordingly, they are suitable for protecting materials that are sensitive to ultraviolet radiation, in particular solar radiation, and comprises an effective photoprotective amount of at least one of the compounds of formulae I or II. In a preferred embodiment of the invention, such compositions are suitable for protecting human skin and/or human hair against the deleterious effects of UV-radiation. In this case, the compositions according to the invention are cosmetic and/or dermatological compositions which comprise, as a carrier, topically applicable, cosmetically acceptable vehicles and diluents.

If appropriate, additional UV-A and UV-B screening agents may be added into the cosmetic and/or dermatological composition of the present invention. The combination of different UV filters may also show synergistic effects.

The total amount of UV screening agents, i.e. of the compounds of general formula I and/or II and additional UV-A/B screening agents, is not critical. Suitable amounts may vary between 0.5 and 20%, preferably between 0.5and 12%, by weight of the total amount of the composition.

Suitable UV-B screening agents which maybe added to the UV-A screening agents of the present invention are the following organic and inorganic compounds:

acrylates, such as 2-ethylhexyl-2-cyano-3,3-diphenylacrylate (octocrylene, PARSOL® 340), ethyl 2-cyano-3,3-diphenylaciate and the like;

camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like;

cinnamate derivatives such as octyl methoxycinnamate (PARSOL® MCX), ethoxyethyl methoxycinnamate, diethanolamine methoxycinnamate (PARSOL® Hydro), isoamyl methoxycinnamate and the like, as well as cinnamic acid derivatives bound to siloxanes;

p-aminobenzoic acid derivatives, such as p-aminobenzoic acid)2-ethylheyl p-dimethylaminobenzoate, N-oxypropylenated ethyl p-aminobenzoate, glyceryl p-aminobenzoate;

benzophenones, such as benzophenone-3, benzophenone-4,2,2', 4,4'-tetrahydroxy-benzophenone, 2,2'-dihydroxy-4,4'-dimethoxybenzophenone and the like;

esters of benzalmalonic acid such as di-(2-ethylhexyl)-4-methoxybenzalmalonate;

esters of 2(4-ethoxy-anilinomethylene)-propandioic acid, such as 2-(4-ethoxy-anilinomethylene)-propandioic acid diethyl ester (EP-A2-0895 776);

organosiloxane compounds containing benzmalonate groups as described in the European Patent Publications EP-B1-0358584, EP-B1-0538431 and EP-A1-0709080;

drometrizole trisiloxane (Mexoryl XL);

pigments such as microparticulated $TiO_2$, and the like, the term "microparticulated" referring to a particle size from about 5 nm to about 200 nm, particularly from about 15 nm to about 100 nm. The $TiO_2$ particles may also be coated by metal oxides such as aluminum or zirconium oxide, or by organic coatings such as polyols, methicone, aluminum stearate, alkyl silane and the like. Such coatings are well known in the art.

Imidazole derivatives such as, e.g., 2-phenyl benzimidazole sulfonic acid and its salts (PARSOL®HS). Salts of 2-phenyl benzimidazole sulfonic acid are, e.g., alkali salts such as sodium- or potassium salts, ammonium salts, morpholine salts, salts of primary, sec. and tert. amines like monoethanolamine salts, diethanolamine salts and the like.

Salicylate derivatives such as isopropylbenzyl salicylate, benzyl salicylate, butyl salicylate, octyl salicylate (NEO HELIOPAN OS), isooctyl salicylate or homomenthyl salicylate (homosalate, HELIOPAN) and the like.

Triazone derivatives such as octyl triazone (UVINUL T-150), dioctyl butamido triazone (UVASORB HEB) and the like.

Suitable conventional UV-A screening agents which may be added to the UV-A screening agents of the present invention are the following organic and inorganic compounds:

Dibenzoylmethane derivatives such as 4-tert.-butyl-4'-methoxydibenzoyl-methane (PARSOL® 1789), dimethoxydibenzoylmethane, isopropyldibenzoylmethane and the like;

benzotriazole derivatives such as 2,2'-methylene-bis-(6-(2H-benzotriazole-2-yl)-4-(1,1,3,3,-tetraznethylbutyl)-phenol (TINOSORB M) and the like;

phenylene-1,4-bis-benzimidazolsulfonic acids or salts such as 2,2-(1,4-phenylene)-bis-(1H-benzimidazol-4,6-disulfonic acid) (Neoheliopan AP);

amino substituted hydroxybenzophenones such as 2-(4-diethylamino-2-hydroxy-benzoyl)-benzoic acid hexylester as described in European Patent Publication EP 1046391;

pigments such as microparticulated ZnO and the like. The term "microparticulated" refers to a particle size from about 5 nm to about 200 nm, particularly from about 15 nm To about 100 nm. The ZnO particles may also be coated by metal oxides such as, e.g., aluminum or zirconium oxides or by organic coatings such as e.g. polyols, methicone, aluminum stearate, alkyl silane. Such coatings are well known in the art.

Because dibenzoylmethane derivatives are photolabile UV-A screening agents, it may be desirable to photostabilize them. Thus, the term "conventional UV-A screening agent" also refers to dibenzoylmethane derivatives such as e.g. PARSOL® 1789 stabilized by, e.g., 3,3-diphenylacrylate derivatives as described in EP-B1-0514491 and EP-A1-0780119;

benzylidene camphor derivatives as described in U.S. Pat. No. 5,605,680;

organosiloxanes containing benzmalonate groups as described in EP-B1-0358584, EP-B1-053843 and EP-A1-0709080.

The compositions of the invention can also contain usual cosmetic adjuvants and additives, such as preservatives/antioxidants, fatty substances/oils, water, organic solvents, silicones, thickeners, softeners, emulsifiers, additional sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, in particular those suitable for providing an additional photoprotective effect by physically blocking out ultraviolet radiation, or any other ingredients usually formulated into cosmetics, in particular for the production of sunscreen/antisun compositions. The necessary amounts of the cosmetic and dermatological adjuvants and additives can, based on the desired product, easily be chosen by the skilled person.

Particularly preferred antioxidants are those chosen from the group consisting of amino acids (e.g. glycine, histidine, tyrosine, tryptophane) and their derivatives, imidazole (e.g urocanic acid) and derivatives, peptides such as D,L-carnosine, D-carnosine, L-carnosine and derivatives (e.g. anserine), carotinoids, carotenes (e.g. β-carotene, γ-carotene, lycopene) and derivatives, chlorogenic acid and derivatives, liponic acid and derivatives (e.g. dihydroliponic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-, oleyl-, γ-linoleyl-, cholesteryl- and glycerylester) and the salts thereof, dilaurylthiodipropionate, distearylthiodipropionate, thiodipropionic acid and its derivatives (esters, ethers, peptides, lipids, nucleotides, nucleosides and salts) as well as sulfoximine compounds (such as buthioninsulfoximine, homocysteinsulfoximine, buthioninsulfone, penta-, hexa-, heptathioninsulfoximine) in very low compatible doses (e.g. from pmol to µmol/kg), additional (metal)-chelators (such as α-hydroxyfatty acids, palmic acid, phytinic acid, lactoferrin), α-hydroxyacids (such as citric acid, lactic acid, malic acid), huminic acid, gallic acid, gallic extracts, bilirubin, biliverdin;, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamine C and derivatives (such as ascorbylpalmitate, Mg-ascorbylpbosphate, Na-ascorbylphosphate, ascorbylacetate), tocopherole and derivates (such as vitamine E acetate), vitamine A and derivatives (vitamine A palmitate) as well as coniferylbenzoat, rutinic acid and derivatives) α-glycosylrutin, ferulic acid, furfurylidenglcitol, carnosin, butylhydroxytoluene, butylhydroxyanisole, trihydoxybutyrophenone, urea and its derivatives; mannose and derivatives, zinc and deivatives (e.g ZnO; $ZnSO_4$), Selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients.

The preservatives and/or antioxidants-may be present in an amount varying from about 0.01 wt. % to about 10 wt. % of the total weight of the composition. Preferably, the preservatives andlor antioxidants are present in an amount varying from about 0.1 wt. % to about 1 wt. %.

The composition according to the present invention may also contain emulsifiers. An emulsifier enables two or more immiscible liquids to be combined homogeneously, while increasing the viscosity of the composition. Moreover, the emulsifier acts to stabilize the composition.

Emulsifiers that may be used according to the present invention, to form O/W, W/O and/or O/W/O formulations, include sorbitan oleate, sorbitan sesquioleate, sorbitan isostearate, sorbitan trioleate, polygyceryl-3-diisostearate, polyglycerol esters of oleic/isostearic acid, polyglyceryl-6 hexaricinolate, polygyceryl-4-oleate, polyglycerol-4 oleate/PBG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof Further suitable emulsifiers are phosphate esters and salts thereof such as cetyl phosphate, DEA cetyl phosphate, potassium cetyl phosphate, sodium glyceryl oleate phosphate, hydrogenated vegetable glyceride phosphates and mixtures thereof Furthermore, one or more synthetic polymers maybe used as emulsifiers. For example, PVP eicosaene copolymer, acrylates/C10-C30 alkyl acrylate crosspolymer, acrylates/steareth methacrylate copolymer, PEG-22/dodecyl glycol copolymer, PEG-45/dodecyl glycol copolymer, and mixtures thereof. The preferred emulsifiers ate PVP eicosaene copolymer, acrylates/C10-C30 alkyl acrylate crosspolymer, PEG-20 sorbitan isostearate, sorbitan isostearate, and mixtures thereof.

The emulsifier is present in a total amount varying from about 0.01 wt. % to about 15 wt. %, preferably from about 0.1 wt. % to about 3 wt. %, of the total weight of the composition.

The fatty/oily phase is advantageously chosen from:
mineral oils and mineral waxes;
oils such as triglycerides of caprinic acid or caprylic acid, preferably castor oil;
natural or synthetic oils, preferably esters of carbonic acids or fatty acids with alcohols, e.g., such as isopropanol, propyleneglycol or glycerine;
alkylbenzoates and
silicone oils such as dimethylpolysiloxane, diethylpolysiloxane, diphenylpolysiloxane and mixtures thereof.

Fatty substances which can be incorporated into the oily phase of the composition according to the invention are advantageously chosen from esters of saturated and/or unsaturated, straight or branched chain alkyl carboxylic acids with 3 to 30 carbon atoms, and saturated and/or unsaturated, straight and/or branched chain alcohols with 3 to 30 carbon atoms, as well as esters of aromatic carboxylic acids and of saturated and/or unsaturated, straight or branched chain alcohols of 3 to 30 carbon atoms. Such esters can advantageously be selected from octylpalmitate, octylcocoate, octylisostearate, octyldodecylmyristate, cetylisononanoate, isopropylmyristate, isopropylpalmitate, isopropylstearate, isopropyloleate, n-butylstearate, n-hexyllaurate, n-decyloleat, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrinmellitate, as well as from synthetic, half-synthetic and natural mixtures of such esters such as jojoba oil.

Other fatty components suitable for use in the composition according to the present invention include polar oils such as lecithines and fatty acid triglycerides, namely triglycerinic esters of saturated and/or unsaturated, straight or branched chain carbonic acids with 8 to 24 carbon atoms, preferably of 12 to 18 carbon atoms whereas the fatty acid triglycerides are preferably chosen from synthetic, half synthetic and natural oils (e.g. cocoglyceride, olive oil, sun flower oil, soybean oil, peanut oil, rape oil, almond oil, palm oil, coconut oil, castor oil, hydrogenated castor oil, wheat oil, grape oil and others); apolar oils such as linear and/or branched chain hydrocarbons and waxes, e.g., mineral oils, vaseline (petrolatum); paraffins, squalan and squalen, polyolefines (favored are polydecenes), hydrogenated polyisobutenes and isohexadecanes; dialkyl ethers such as dicaprylylether; linear or cyclic silicone oils such as cyclomethicone, octametlylcyclotetrasiloxane, cetyldimethicone, hexamethylcyclotrisiloxane, polydimethylsiloxane, poly-(methylphenylsiloxan) and mixtures thereof Other fatty components which can advantageously be incorporated into the composition of the present invention are isoeikosane; neopentylglycoldiheptanoate; propylenglykol-dicaprylate/-dicaprate; caprylic-/capric-/diglycerylsuccinate; butylenglykol caprylat/caprat; C12-13 alkyllactate; di-C12-13 alkyltartrate; triisostearin; dipentaerythrityl hexacaprylat/hexacaprate; propylglykolmonoisostearate; tricaprylin; dimethylisosorbid. Particularly preferred is the use of mixtures of C12-15 alkylbenzoate and 2-ethylhexylisostearate, mixtures of C12-15 alkylbenzoate and isotridecylisononanoate as well as mixtures of C12-15 alkylbenzoate, 2-ethylhexylisostearate and isotridecylisononanoate.

The oily phase of the composition according to the present invention can also contain natural vegetable or animal waxes such as bee wax, china wax, bumblebee wax and other waxes of insects as well as sheabutter.

The composition according to the present invention may additionally contain one or more emollients. An emollient provides a softening or soothing effect on the skin surface and is generally considered safe for topical use. Emollients also help control the rate of evaporation and the tackiness of the composition. Preferred emollients include mineral oil, lanolin oil, coconut oil, cocoa butter, olive oil, aloe extracts, jojoba oil, castor oil, fatty acids such as oleic and stearic acid, fatty alcohols such as cetyl and hexadecyl alcohol diisopropyl adipate, benzoic and hydroxybenzoic acid esters of $C_9$-$C_{15}$ alcohols, isononyl iso-nonanoate, $C_{15}$-$C_{50}$ alkanes, mineral oil, silicones such as dimethyl polysiloxane, ethers such as polyoxypropylene butyl ethers and polyoxypropylene cetyl ethers, and $C_2$-$C_{15}$ alkyl benzoates, and mixtures thereof. The most preferred emollients are hydroxybenzoate esters, aloe vera, $C_{12-15}$ alkyl benzoates, and mixtures thereof.

The emollient is present in an amount varying from about 1 wt. % to about 20 wt. %, preferably from about 2 wt. % to about 15 wt %, and most preferrably from about 4 wt. % to about 10 wt. % of the total weight of the composition.

The aqueous phase of the formhulation of the present invention can contain the usual cosmetic additives such as alcohols, especially lower alcohols, preferably ethanol and/or isopropanol, low alkyl diols or polyols and their ethers, preferably propyleneglycol, glycerine, ethyleneglycol, ethyleneglycolmonoethyl- or -monobutyl ether, propyleneglycol-monomethyl-, -monoethyl- or -monobutyl ether, diethyleneglycolmonomethyl- or -monoethyl ether and analogue products, polymers, foam stabilisators; electrolytes and, especially, one or more thickeners.

Thickeners that may be used in formulations of the present invention include the family of silicium dioxide, magnesium and/or aluminum silicates, polysaccharides and their derivatives such as hyaluronic acid, xanthan gum, hydroxypropyl cellulose, acrylate copolymers, preferably a polyacrylate of the family of carbopoles, such as carbopoles of is type 980, 981, 1382, 2984, 5984.

Moisterizing agents, such as humectants, maybe incorporated into the composition according to the present invention to reduce the trans-epidermal water loss (TEWL) of the horny layer of the skin. Suitable humectants include glycerin, lactic acid, pyrrolidone carbonic acid, urea, polyethylene glycol, polypropylene glycol, sorbitol, PEG-4, and mixtures thereof. Additional suitable moisturizers are polymeric moisturizers of the familiy of water soluble and/or with water gelating polysaccarides such as hyaluronic acid, chitosan and/or fucose rich polysaccharides available, e.g., as Fucogel®1000 (CAS-Nr. 178463-23-5) from SOLABIA S. The moisterzing agent is optionally present in an amount varying from about 0.5 wt % to about 8 wt. %, preferably from about 1 wt. % to about 5 wt. % of the total weight of the composition.

Suitable neutralizing agents may also be included into the composition of the present invention such as emulsifiers, foam builders and stabilizers. Suitable neutralizing agents include alkali hydroxides such as sodium or potassium hydroxide; organic bases such as diethanolamine, triethanolamine, aminomethyl propanol, trisodium ethylenediaminetetraacetic acid; basic amino acids such as arginine and lysine; and any combination of any of the foregoing. The neutralizing agent is optionally present in an amount from about 0.01 wt. % to about 8 wt. %, preferably from 1 wt % to about 5 wt. %, of the total weight of the composition.

The addition of electrolytes into the composition of the present invention is preferred to change the behavior of a hydrophobic emulsifier. Thus, the microemulsions of this invention contain preferably electrolytes of one or several salts with anions including but not limited to chlorides, sulfates, carbonates, borates and aluminates. Other suitable electrolytes can be on the basis of organic anions such as, but not limited to, lactates, acetates, benzoates, propionates, tartrates and citrates. Preferred cations are ammonium, alkylammonium, alkali metals, magnesium, iron and zinc ions. Particularly preferred salts are potassium and sodium chloride, magnesium sulfate, zinc sulfate and mixtures thereof The electrolytes are present in an amount varying from about 0.01 wt. % to about 8 wt. % of the total weight of the composition.

The compositions according to the present invention are useful for photoprotecting the human epidermis or hair against the damaging effect of ultraviolet irradiation, as anti-sun/sunscreen compositions or as makeup products. Such compositions can particularly be provided in the form of a lotion, a thickened lotion, a gel, a cream, a milk, an ointment, a powder or a solid tube stick and can optionally be packaged as an aerosol and can be provided in the form of a mousse, foam or a spray. They can be in the form of a suspension or dispersion in solvents or fatty substances, or alternatively in the form of an emulsion, preferably of the O/W type, such as a cream or a milk, a vesicular dispersion, in the form of an ointment, a gel, a solid tube stick or an aerosol mousse. The emulsions can also contain anionic, nonionic, cationic or amphoteric surfactants.

When the cosmetic compositions according to the invention are used for protecting the hair, they can be in the form of a lotion, a gel or a rinse out composition like a shampoo or a conditioner, to be applied before or after shampooing, before or after dyeing or bleaching, before, during or after permanent-waving or hair straightening operation, a styling or treatment lotion or a gel, a blow-drying or hairsetting lotion or gel, a hair lacquer, or a composition for permanent-waving, straightening, dyeing or bleaching the hair.

The invention is further illustrated by the following examples.

EXAMPLE 1

2-(4-Benzoxazol-2-yl-benzylidene)-malonic acid diethyl ester

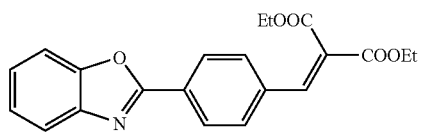

a) Diethyl-p-carboxy-benzalmalonate

A 500 ml three necked reaction flask, equipped with a reflux condenser combined with a water separator and an oil bath with a magnetic stirrer was charged with 24.8 g (170 mmol) of 4-carboxy-benzaldehyde (Fluka), 26.3 g (170 mmol) of diethylialonate, 1.3 g of morpholine and 1.4 g of p-toluene-sulfonic acid in 300 ml of toluene. After two hours under reflux 3 ml of water were separated. The reaction mixture was diluted with ethylacetate and washed with aqueous $NH_4Cl$ and NaCl solutions, dried with $Na_2SO_4$ and concentrated to yield a brown honey. Recrystallization from toluene furnished 18 g of brown crystals. M.p. 100-102° C. UV(ethanol) 286 nm (E=24'800)

b) 2-(4-Benzoxazol-2-yl-benzylidene)-malonic acid diethyl ester 10 g of phosphorpentoxide, 25 ml of hexamethyldisiloxane and 50 ml of 1,2-dichlorobenzene were mixed in a 250 ml round bottom flask and refluxed for a few minutes, until the mixture became clear.

1.5 g of the diethyl-p-carboxy-benzalmalonate obtained above and 0.66 g of 2-aminophenol were dissolved in 15 ml of the clear phosphorpentoxide mixture and refluxed for four hours. Then the cold reaction mixture was diluted with 150 ml of ethyl acetate and extracted with in NaOH and aqueous NaCl solutions. The organic phase was dried with $Na_2SO_4$ and concentrated to yield 1 g of brown crystals, which there chromatographed through silicagel in hexane:ethylacetate=3:1, v/v). 0.77 g of product in form of yellow crystals were obtained. M.p. 99-102° C. UV($CH_2Cl_2$)331 nm (E=1010); MS: 365 (M$^+$), 320, 291, 275, 247, 219 (100%).

Solubility Measurement

An excess of the UV sunscreen was placed in a flask, containing Cétiol LC (cocoyl caprylate caprate) and Crodamol DA (diisopropyl adipate), respectively. The suspension was mixed and treated in an ultrasound bath for 10 minutes. After standing at room temperature for 18 hours, the solution over the remaining crystals was filtered through a millipore microfilter (pore size of 0.45 µm). The concentration of this saturated solution was determined by means of UV spectroscopy in comparison with a calibration curve.

The solubility of this product was found to be 4.5% in Cétiol LC and 11% in Crodamol DA.

Photostability:

The photostability is measured in an on-line system Hg-lamp/HPLC, using a 150 W Hg-lamp of Heraeus with Pyrex filter (2.3 mm) and a Teflon capillary tube with 0.3 mm inside diameter and a total length of 10 m. 3.6. mg of the sample is dissolved in 16 ml of MeOH and 10 µl of this solution injected. The degradation products are not separated. UV-absorption at a wavelength of 358 nm of the irradiated solution is measured periodically up to 14 minutes and the result is compared with the corresponding photostability of butyl methoxy dibenzoylmethane. The product was detected in >90%, indicating photostability, whereas only 16% of butyl methoxy dibenzoylmethane could be detected after 14 minutes of irradiation.

Alternatively, the measurement is performed according to the protocol described in the *International Journal of Cosmetic Science* 18, 167-177 (1996).

EXAMPLE 2

2-Cyano-3-{4-[5-tert.-butyl-benzoxazol-2-yl]-phenyl}-acrylic acid 2-ethylhexyl ester

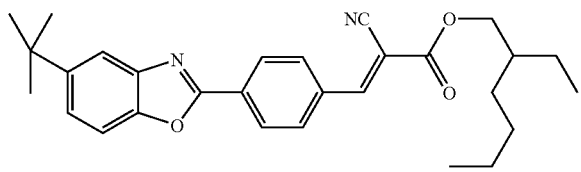

a) 2-Cyano-{p-carboxy-phenyl}-acrylic acid 2-ethylhexyl ester

A 250 ml three necked reaction flask, equipped with a reflux condenser combined with a water separator and an oil bath with a magnetic stirrer was charged with 3.8 g (25 mmol) of 4-carboxy-benzaldehyde (Fluka), 6.8 g (33 mmol) of cyanacetic-acid-2-ethyl-hexylester, 0.3 g of bis-(2-hydroxypropyl)-amine and 0.25 g of p-toluene-sulfonic acid in 80 ml of toluene and 20 ml of dimethylformamide. After 22 hours under reflux the reaction mixture was diluted with toluene and washed with aqueous NH$_4$Cl and NaCl solutions, dried with Na$_2$SO$_4$ and concentrated to yield 6.2 g (74%) of whire crystals. M.p. 159-162° C. W(CH$_2$C$_2$) 305 nm (E=811).

b) 2-Cyano-3-{4-[5-tert.-butyl-benzoxazol-2-yl]-phenyl-}-acrylic acid 2-ethylhexyl ester 3.6 g of the 2-cyano-{p-carboxy-phenyl}-acrylic acid 2-ethylhexyl ester obtained above and 2.5 g of 2-amino-4-tert.-butyl-phenol were dissolved in 16 ml of the clear phosphorpentoxide mixture (described in Example 1b) and refluxed for four hours. Then the cold reaction mixture was diluted with 100 ml of chloroform and 3× extracted with In NaOH and 1× with aqueous NaCl solution. The organic phases were dried with Na$_2$SO$_4$ and concentrated to yield a brown honey, which was washed with pentane and dried under high vacuum. 1.02 g of brown crystals of product were obtained. M.p. 80-81° C. UV(CH$_2$C$_2$) 363 nm (E=816); MS: 458 (M+), 443(100%), 409, 346, 331.

The solubility of this product was determined in Cétiol LC=3.8% and in CrodaMol DA=7.4%. The product was irradiated in high dilution with a Hg-lamp 150 W from Heraeus and has been shown to be photostable.

EXAMPLE 3

2-(4-Benzoxazol-2-yl-benzylidene)-malonic acid dibutyl ester

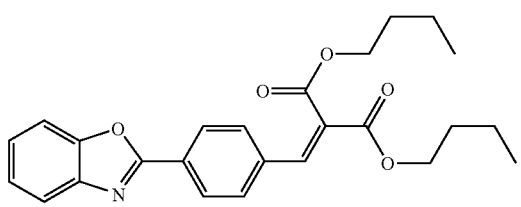

a) 2-p-Toluyl-benzoxazole

A 350 ml three necked reaction flask was charged under nitrogen atmosphere with 40.8 g of p-toluylic acid, 33 g of o-aminophenol and 1.5 g of H$_3$BO$_3$ in 120 ml of diethyleneglycol-diethyl ether and 30 ml of diethyleneglycol-dibutyl ether. This mixture was heated first to 180° C., until a slow distillation starts. Then it was heated further to 220° C. for 10 hours, until practically no starting material was visible on the tlc. At this stage 90 ml of the solvent was distilled off. The cold, crystalline residue-was dissolved in ethylacetate and washed subsequently with in NaOH, In HCl and saturated aqueous NaCl. The organic phase was dried and concentrated. The crystalline material was washed with hexane and dried under high vacuum to yield 29.5 g of brown crystals. M.p. 104-105° C. UV: (CH$_2$Cl$_2$) 303 nm (E=1323).

b) 4-Benzoxazol-2-yl-benzaldehyde

A 750 ml round bottom flask equipped with a magnetic stirrer, a reflux condenser and an ice cooling bath under nitrogen atmosphere was charged with 22 g of 2-p-toluyl-benzoxazole dissolved in 200 ml of acetic anhydride. This mixture was cooled to −5° C. and 44.5 ml of concentrated sulfuric acid was slowly added by means of a dropping funnel, while the temperature was kept below 0° C. Then a solution of 15.3 g of CrO$_3$ dissolved in 200 ml of acetic anhydride was slowly added at the same temperature. The green mixture was left over night with stirring and then poured on ice. The precipitate was filtered off, washed with water and dried under high vacuum to yield 18.6 g of aldehyde in crystalline form, containing some traces of starting material. M.p. 162-163° C. UV(CH$_2$Cl$_2$) 324 nm (E=1233).

When the reaction mixture was immediately worked up after the addition of the CrO$_3$ solution, mainly (ca. 73% content) 4-benzoxazol-2-yl-benzaldehyde-diacetylacylal was obtained. UV(CH$_2$Cl$_2$) 302 nm (E=964).

c) 2-(4-Benoxazol-2-yl-benzylidene)-malonic acid dibutyl ester

A 50 ml three necked reaction flask, equipped with a reflux condenser combined with a water separator and an oil bath with a magnetic stirrer, was charged with 2.3 g (10 mmol) of 4-benzoxazol-2-yl-benzaldehyde, 2.6 g (1.1 mmol) of di-n-butylmalonate, 0.25 ml of morpholine and 0.17 g of p-toluene-sulfonic acid in 30 ml of xylene. After five days under reflux mainly the desired product was detected with HPLC. The reaction mixture was diluted with ethylacetate and washed with water and NaCl solution, dried with Na$_2$SO$_4$ and concentrated to yield 4.9 g of a brown honey. Chromatography in hexane/ethylacetate (9:1 to 1:1, v/v) and furnished 1.5 g of a yellow liquid. UV(ethanol) 329 nm (E=758), MS: 421 (M$^+$,100%).

This product is miscible with Cétiol LC. It was irradiated in high dilution with a Hg-lamp 150 W from Heraeus and has been shown to be photostable.

EXAMPLE 4

2-Cyano-3-{4-benzoxazol-2-yl-phenyl}-acrylic acid 2-ethylhexyl ester

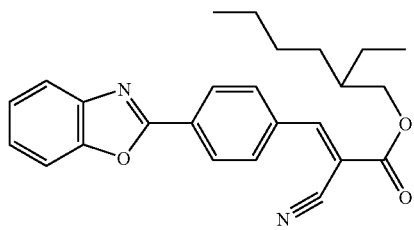

A 50 ml three necked reaction flask, equipped with a reflux condenser and an oil bath with a magnetic stirrer was charged with 2 g of 4-benzoxazol-2-yl-benzaldehyde-diacetylacylal (73% product content, described in Example 3b), 1.0 ml of cyanacetic-acid-2-ethyl-hexylester and 0.31 g of dry $ZnCl_2$ in 15 ml of toluene. This mixture was heated for 20 hours to 50° C. Then water and NaOH was added to reach a pH of 9. The organic phase was diluted with ethylacetate and washed with water and NaCl solution, dried with $Na_2SO_4$ and concentrated. The residue was chromatographed in hexane/ethylacetate (9:1 to 1:1, v/v) and then recrystallised from hexane and toluene and furnished 0.7 g of yellowish crystals of 2-cyano-3-{4-[benzoxazol-2-yl]-phenyl}-acrylic acid 2-ethylhexyl ester. M.p. 84-85° C.; UV(CH$_2$Cl$_2$) 355 nm (E=964); MS: 402 (M$^+$), 290 (100%), 273, 246.

The solubility of this product was determined in Cétiol LC=1.6% and in Crodamol DA=2.8%. The product was irradiated in high dilution with a. Hg-lamp 150 W from Heraeus and has been shown to be photostable after E/Z isomerisation.

EXAMPLE 5

3-{4-Benzoxazol-2-yl-phenyl}-2-propionyl-acrylic acid 2-ethylhexyl ester

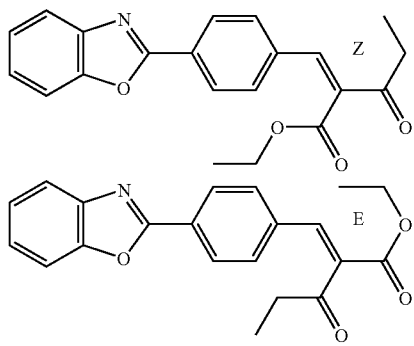

The same reaction as in Example 4 was performed, but instead of cyanacetic-acid-2-ethyl-hexylester, ethyl-3-oxo-valerate was used. After chromatography an E- and a Z-product was obtained. Data of the Z-product: M.p. 82-83° C.; UV(CH$_2$Cl$_2$) 334 nm (E=1083); MS: 349 (M$^+$), 334, 320 (100%), 292, 252.

The product eras irradiated in high dilution with a Hg-lamp 150 W from Heraeus and has been shown to be photostable after E/Z isomerisation.

EXAMPLE 6

2-(4-[6-Hydroxy-benzoxazol-2-yl]-benzylidene)-malonic acid diethyl ester

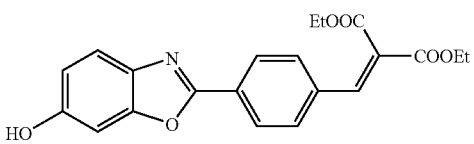

The same reaction was performed as in Example 1b, but instead of 2-aminophenol, 4-amino-resorcinol was applied. Instead of chromatography, the raw material was recrystallised three times from acetonitrile, hexane and CH$_2$Cl$_2$ to yield 12% of yellow crystals. M.p. 153-55° C. UV(CH$_2$Cl$_2$) 346 nm (E=851); MS: 381 (M$^+$, 100% 336, 307, 291, 263, 235.

The solubility of this product was determined in Crodamol DA=1.6%. The product was irradiated in high dilution with a Hg-lamp 150 W from Heraeus and has been shown to be photostable.

EXAMPLE 7

2-(4-[6-{2-Ethyl-hexyloxy-benzoxazol-2-yl]-benzylidene)-malonic acid diethyl ester

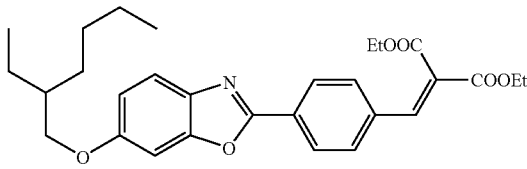

A 50 ml three necked reaction flask, equipped with a reflux condenser and an oil bath with a magnetic stirrer was charged with 0.7 g of 2-(4-[6-hydroxy-benzoxazol-2-yl]-benzylidene)-malonic acid diethyl ester (described in Example 6), 0.34 ml of 2-ethyl-hexyl-1-bromide and 0.5 g of anhydrous. Na$_2$CO$_3$ in 10 ml of 1-methyl-2-pyrrolidone. A trace of each, KJ and tetrabutylammonium-sulfate was added, After 20 hours at 100° C., no starting material could be seen on the tlc. The reaction mixture was diluted with ethylacetate and washed with InNaOH, water and NaCl solution, dried with Na$_2$SO$_4$ and concentrated. Then it was chromatographed in hexane/ethylacetate (9:1 to 1:1, v/v) and furnished 300 mg of light yellow crystals. M.p. 50-52° C.; UV(ethanol) 352 nm (E=695); MS: 493 (M$^+$), 381 (100%), 307, 235.

The solubility of this product was determined in Cétiol LC (Cocoyl caprylate caprate)=10.2% It was irradiated in high dilution with a Hg-lamp 150 W from Heraeus and has been shown to be photostable.

EXAMPLE 8

2-(4-{6-[2(2-Ethoxy-ethoxy)ethoxy-benzoxazol-2-yl}-benzylidene)-malonic acid diethyl ester

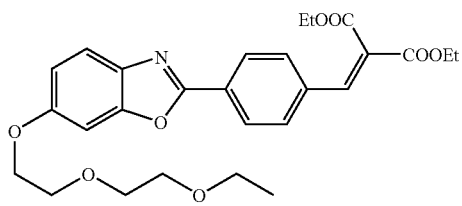

The same reaction was performed as in Example 7, but instead of 2-ethyl-hexyl-1-bromide, 2-(2-ethoxy-ethoxy)-ethoxy-methylsulfonate was applied. After work up the product was chromatographed with hexane/diethylether (9:1 to 1:1, v/v) to yield a yellowish oil, which crystallised only after a two months time. M.p. 43-45° C.; UV(CH$_2$Cl$_2$) 341 nm (E=551); MS: 497 (M$^+$, 100%). 452, 381.

The solubility of this product was determined in Cétiol LC=4.6%. The product was irradiated in high dilution with a Hg-lamp 150 W from Heraeus and has been shown to be photostable.

EXAMPLE 9

2-(4-{6-[2-(Methyl-bis-(trimethyl-silyloxy)-silyloxy)-prop-2-enyloxy]benzoxazol-2-yl}-benzylidene)-malonic acid diethyl ester

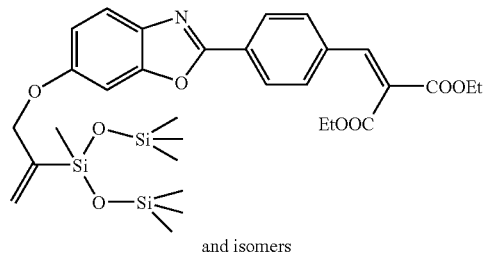

and isomers a) 2-(4-[6-{2-Propargyloxy}-benzoxazol-2-yl]-benzylidene)-malonic acid diethyl ester The same reaction was performed as in Example 7, but instead of 2-ethyl-hexyl-1-bromide, propargylbromide was applied. After work up the product was chromatographed with hexane/ethylacetate (9:1 to 1:1, v/v) to yield yellow crystals. M.p. 105-107° C.; UV(CH$_2$Cl$_2$) 345 nm (E=875); MS: 419 (M$^+$), 380 (100%), 374, 306, 234.

b) 2-(4-{6-[2-(methyl-bis-(trimethyl-silyloxy)-silyl)-prop-2-enyloxy]-benzoxazol-2-yl}-benzylidene)-malonic acid diethyl ester (hydrosilylation reaction)

200 mg of the 2-(4-[6-{2-propargyloxy}-benzoxazol-2-yl]-benzylidene)-malonic acid diethyl ester (Example 9a, above), 125 mg of 1,1,1,3,5,5,5-heptamethyl trisiloxane and a catalytic amount of divinyl-tetramethyl disiloxane platinum complex in 5 ml of toluene was placed in a three-necked reaction flask under inert atmosphere, stirred for 20 hours at 80° C. and then two days under reflux. The product solution was washed with a mixture of water/methanol, 1:10, v/v and concentrated. This product was chromatographed in hexane/ethylacetate 9:1, v/v to yield a honey-like liquid. WV 348 nm (E=535). NMR showed a mixture of the vicinal and the geminal hydrosilylation product=1.3. It has an unlimited solubility in the cosmetic solvents tested above and excellent photostability qualities in high dilution.

EXAMPLE 10

A Polysiloxane Which Corresponds Statistically to the Following Formula

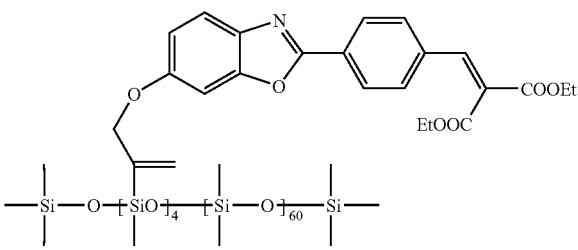

200 mg of the 2-(4-[6-{2-propargyloxy}-benzoxazol-2-yl]-benzylidene)-malonic acid diethyl ester (Example 9a, above), 530 mg of polysiloxane Ae-151 of Wacker-Chemie GmbH and a catalytic amount of platinum on carbon 5% in 10 ml of xylene was placed in a three-necked reaction flask under inert atmosphere and heated for five days to 120° C. The product solution was filtered through Cellite, washed with a mixture of water/methanol, 1:10, v/v and concentrated to yield a brownish oil. UV 348 nm (E=207), having unlimited solubility in Cétiol LC and Crodamol DA and excellent photostability qualities in high dilution.

EXAMPLE 11

Preparation of a O/W Sunscreen Lotion UV-B and UV-A

Broad spectrum sunscreen lotion containing 2% of the compound of Example 1.

| Recipe % | Compound | Chemical Name |
|---|---|---|
| Part A | | |
| 2 | PARSOL MOX | Ethylhexyl methoxycinnamate |
| 2 | Product of Example 1 | |
| 3 | PARSOL 1789 | 4-t-Butyl-4'-methoxy-dibenzoyl-methane |
| 12 | Cétiol LC | Cocoyl-caprylate caprate |
| 4 | Dermol 185 | Isostearyl neopentanoate |
| 0.25 | PEG-2-stearate | Diethyleneglycol monostearate |
| 1 | Cetylalcohol | Cetylalcohol |
| 0.25 | MPOB/PPOB | Methyl-propylparabene |
| 0.1 | EDTA BD | EDTA-sodium salt |
| 1 | Amphisol DEA (Givaudan) | Diethanolamine cetylphosphate |
| Part B | | |
| 0.2 | Permulene TR-1 | Acrylate C10-C30 Alkylacrylate |
| 68.4 | Water deionized | |
| 5 | Propyleneglycol | 1,2-Propanediol |
| 0.8 | KOH (10%) | Potassium hydroxide |

Part A is heated in a reactor to 85° C.
Part B is slowly added within 10 minutes, followed by addition of KOH, cooling and degassing of the emulsion.

EXAMPLE 12

Preparation of a High Protective Sun Milk

| | Ingredients | NCI Nomenclature | % w/w |
|---|---|---|---|
| A) | PARSOL SLX | Dimethico Diethylbenzalmalonate | 6.00 |
| | PRODUCT OF EXAMPLE 10 | | 6.00 |
| | Parsol 5000 | 4-Methylbenzylidene camphor | 4.00 |
| | Parsol MCX | Ethylhexyl methoxicinnamate | 6.00 |
| | Uvinul T 150 | | 2.00 |
| | Silicone DC 200/350 cs | Dimethicone | 1.00 |
| | Lanette O | Cetyl alcohol | 2.00 |
| | Softisan 100 | Hydrogenated coco-glycerides | 3.00 |
| | Tegosoft TN | C12-15 Alkyl benzoate | 6.00 |
| | Cetiol B | Dibutyl adipate | 7.00 |
| | Vitamin E acetate | Tocopheryl acetate | 2.00 |
| | Berkemyol (Grape Seed) | Palmitoyl grape seed extract | 1.00 |
| | BHT | BHT | 0.05 |
| | Edeta BD | Disodium EDTA | 0.10 |
| | Phenonip | Mixture of phenoxyethanol, methylparaben, ethylparaben, propylparaben and butylparaben | 0.60 |
| | AMPHISOL K | Potassium cetyl phosphate | 2.00 |
| B) | Water deionized | | 44.45 |
| | Propylene Glycol | Propyleneglycol | 5.00 |
| | Carbopol 980 | Carbomer | 0.30 |
| C) | KOH (10% sol.) | Potassium hydroxide | 1.50 |

The invention claimed is:
1. A compound of general formula I

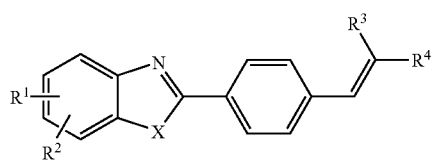

wherein
$R^1$ and $R^2$ are, independently from each other, hydrogen; halogen; hydroxy; $(C_1-C_{20})$-alkyl; $(C_2-C_{20})$-alkenyl; or $(C_1-C_{20})$-alkoxy;
X is oxygen or an imino group, optionally substituted with $R^1$;
$R^3$ and $R^4$ are, independently from each other, cyano; —COOR$^5$; —COR$^6$; —CONH$_2$; —CONHR$^7$; or —CONR$^8$R$^9$;
$R^5$, $R^6$, $R^7$, $R^8$ and $R^9$ are, independently from each other, hydrogen; $(C_1-C_{20})$-alkyl, wherein one or more methylene groups are optionally replaced by one or more oxygens; $(C_1-C_{20})$-haloalkyl; $(C_2-C_{20})$-alkenyl, optionally substituted by tri-$(C_1-C_5)$-alkylsilyl, triphenylsilyl or a group —Si[CH$_3$]$_n$[OSi(CH$_3$)$_3$]$_{3-n}$, wherein n is 0, 1, 2 or 3.

2. A compound according to claim 1 wherein X is O.
3. A compound according to claim 1 wherein $R^1$ and $R^2$ are hydrogen.
4. A compound according to claim 1 wherein $R^3$ cyano and $R^4$ is —COOR$^5$.
5. A compound according to claim 4 which is:
2-cyano-3-{4-[5-tert.-butyl-benzoxazol-2-yl]-phenyl}-acrylic acid 2-ethylhexyl ester or
2-cyano-3-{4-benzoxazol-2-yl-phenyl}-acrylic acid 2-ethylhexyl ester.
6. The compound according to claim 1, wherein $R^3$ and $R^4$ are, independently from each other, —COOR$^5$.
7. A compound according to claim 6 which is:
2-(4-benzoxazol-2-yl-benzylidene)-malonic acid diethyl ester;
2-(4-benzoxazol-2-yl-benzylidene)-malonic acid dibutyl ester;
3-{4-benzoxazol-2-yl-phenyl}-2-propionyl-acrylic acid 2-ethylhexyl ester;
2-(4-[6-hydroxy-benzoxazol-2-yl]-benzylidene)-malonic acid diethyl ester;
2-(4-[6-{2-ethylhexyl-oxy}-benzoxazol-2-yl}-benzylidene)-malonic acid diethyl ester; or
2-(4-[6-[2-(2-ethoxy-ethoxy)-ethoxy]-benzoxazol-2-yl}-benzylidene)-malonic acid diethyl ester.
8. A composition comprising a compound according to claim 1 and at least one pharmaceutically and/or cosmetically acceptable excipient.
9. A composition according to claim 8, wherein the compound according to claim 1 is present in an amount varying between 0.5 and 20% by weight of the total amount of the composition.
10. A composition according to claim 9 wherein the compound according to claim 1 is present in an amount varying between 0.5 and 12% by weight of the total amount of the composition.
11. A composition according to claim 8 which is a topical composition.
12. A composition according to claim 9 which is a topical composition.
13. A composition according to claim 10 which is a topical composition.
14. A method for protecting human skin or human hair from UV-A irradiation comprising applying a photoprotective amount of a compound according to claim 1 to the human skin or human hair.
15. A method for protecting a plastic material or a medicinal product that is sensitive to UV radiation from UV-A irradiation comprising applying a photoprotective amount of a compound according to claim 1 to the plastic material or medicinal product.

* * * * *